(12) United States Patent
Govari et al.

(10) Patent No.: US 8,706,193 B2
(45) Date of Patent: Apr. 22, 2014

(54) CATHETER WITH OBLIQUELY-ORIENTED COILS

(75) Inventors: Assaf Govari, Haifa (IL); Dror Levy, Kiryat Tivon (IL)

(73) Assignee: Biosense Webster, Inc.

( * ) Notice: Subject to any disclaimer, the term of this patent is extended or adjusted under 35 U.S.C. 154(b) by 634 days.

(21) Appl. No.: 12/488,692

(22) Filed: Jun. 22, 2009

(65) Prior Publication Data

US 2010/0324412 A1    Dec. 23, 2010

(51) Int. Cl.
   *A61B 5/00*    (2006.01)
(52) U.S. Cl.
   USPC ........................................... 600/424
(58) Field of Classification Search
   None
   See application file for complete search history.

(56) References Cited

U.S. PATENT DOCUMENTS

| | | | |
|---|---|---|---|
| 6,233,476 B1 * | 5/2001 | Strommer et al. | 600/424 |
| 6,253,770 B1 * | 7/2001 | Acker et al. | 128/899 |
| 6,690,963 B2 | 2/2004 | Ben-Haim et al. | |
| 2003/0129750 A1 * | 7/2003 | Schwartz | 435/377 |
| 2005/0245814 A1 | 11/2005 | Anderson et al. | |
| 2006/0116571 A1 | 6/2006 | Maschke et al. | |
| 2007/0016007 A1 * | 1/2007 | Govari et al. | 600/424 |
| 2007/0079660 A1 * | 4/2007 | Feller | 73/861.27 |
| 2009/0115406 A1 | 5/2009 | Anderson et al. | |

FOREIGN PATENT DOCUMENTS

| EP | 1472976 A1 | 11/2004 |
|---|---|---|
| EP | 2 238 901 A2 | 10/2010 |

OTHER PUBLICATIONS

EP Search Report EP 10 25 1118 Dated Nov. 23, 2010.

* cited by examiner

*Primary Examiner* — Long V. Le
*Assistant Examiner* — Lawerence Laryea

(57) ABSTRACT

A medical probe includes an elongate body having a longitudinal axis, and a plurality of magnetic field transducers, which are contained within the body and have respective transducer axes that are oriented obliquely with respect to the longitudinal axis.

17 Claims, 4 Drawing Sheets

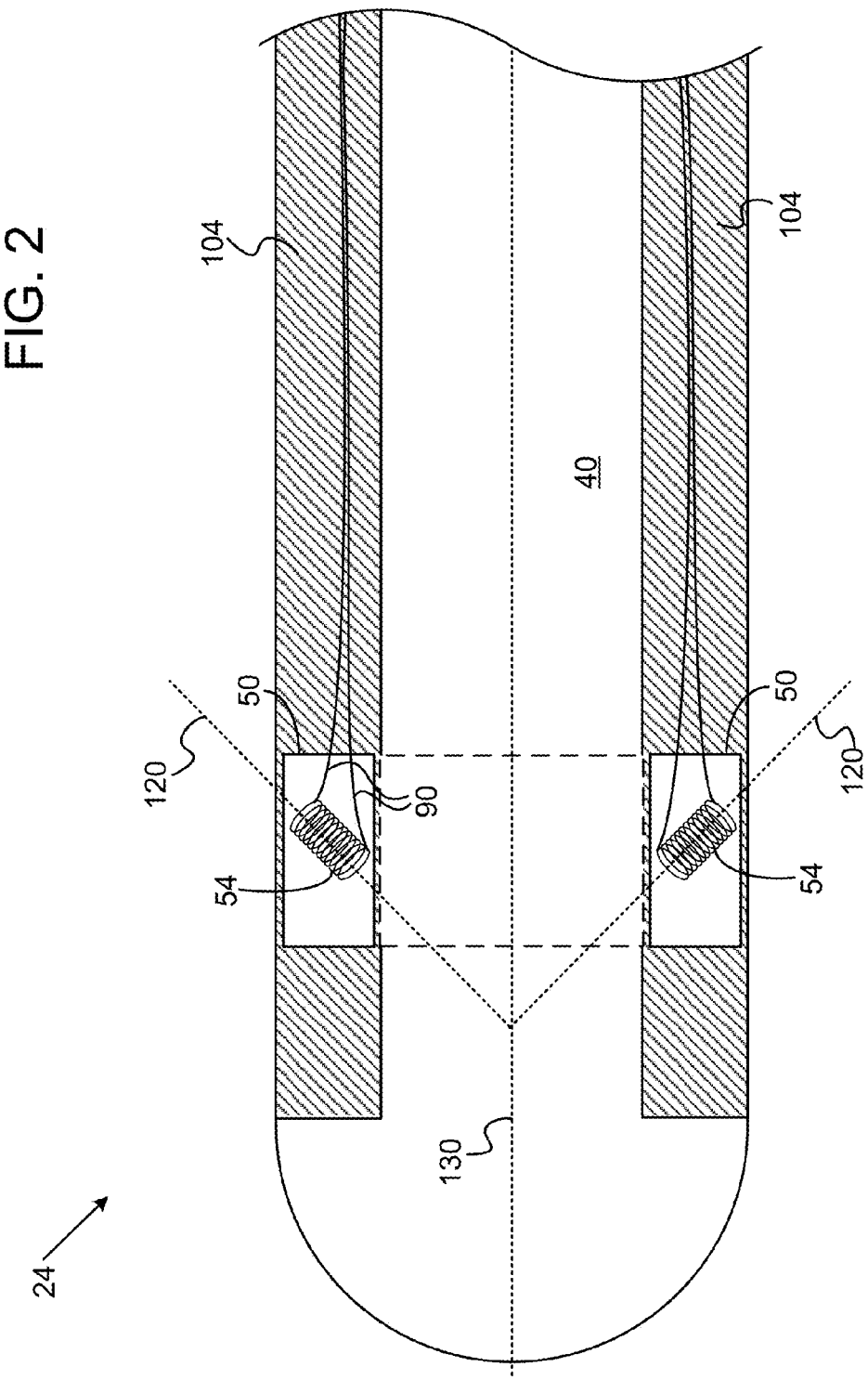

CATHETER WITH OBLIQUELY-ORIENTED COILS

FIELD OF THE INVENTION

The present invention relates to medical instruments, and particularly to intra-body medical instruments equipped with position sensors.

BACKGROUND OF THE INVENTION

Intra-body probes, such as catheters, are used in various medical applications. Such probes include, for example, balloon angioplasty catheters, catheters for laser-, electrical- or cryo-ablation, probes used for nearly incision-less surgery or diagnosis, and endoscopes. Such probes are sometimes equipped with position sensors that enable an external system to measure their location within a patient's body.

For example, U.S. Pat. No. 6,690,963, whose disclosure is incorporated herein by reference, describes a catheter comprising a locating sensor at the distal end. The locating sensor comprises two or three antennas, for example coils, which are irradiated by two or three radiators, for example coils, located outside the body surface of the patient. The three radiators are driven by radiator drivers. The signals received by the receiving antennas are amplified and processed, together with a representation of the signals used to drive the radiators, to provide a display, or other indication, of the position and orientation of the distal end of the catheter.

U.S. Pat. No. 6,253,770, whose disclosure is incorporated herein by reference, describes a catheter having a lumen, which is obstructed by a portion of the catheter. The catheter includes a position detector at the tip of the catheter.

SUMMARY OF THE INVENTION

An embodiment of the present invention provides a medical probe, including an elongate body having a longitudinal axis; and a plurality of magnetic field transducers, which are contained within the body and have respective transducer axes that are oriented obliquely with respect to the longitudinal axis.

In some embodiments, the elongate body includes an insertion tube for insertion into an organ of a patient. In a disclosed embodiment, the plurality of transducers includes three transducers. In an embodiment, the transducers are substantially mutually orthogonal. In another embodiment, the transducers are positioned within the elongate body so that none of the transducers intersects the longitudinal axis. In yet another embodiment, the elongate body contains a central lumen along the longitudinal axis, and the transducers are positioned so as not to impinge on the central lumen. In still another embodiment, the transducers are positioned at a distal end of the elongate body, and the probe includes leads connecting the transducers to a connector located at a proximal end of the elongate body. In some embodiments, the probe includes a cylinder-shaped fixture for holding the transducers within the elongate body, the fixture having a central opening that is parallel with the longitudinal axis. In an embodiment, the field transducers include coils.

There is additionally provided, in accordance with an embodiment of the present invention, a medical position tracking system, including a medical probe, including an elongate body having a longitudinal axis; and a plurality of magnetic field transducers, which are contained within the body and have respective transducer axes that are oriented obliquely with respect to the longitudinal axis and a position measurement subsystem, which is arranged to exchange one or more magnetic fields with the magnetic field transducers in the probe, and to compute a position of the probe responsively to the exchanged fields.

In an embodiment, the transducers include field detectors, which are positioned at a distal end of the elongate body and are operative to sense one or more magnetic fields generated by the position measurement subsystem in a vicinity of the distal end and to produce, responsively to the sensed fields, respective electrical signals that are indicative of the position of the distal end. In an alternative embodiment, the transducers include field generators, which are positioned at a distal end of the elongate body and are operative to generate one or more magnetic fields for sensing by the position measurement subsystem, such that the fields sensed by the position measurement subsystem are indicative of the position of the distal end.

The present invention will be more fully understood from the following detailed description of the embodiments thereof, taken together with the drawings in which:

BRIEF DESCRIPTION OF THE DRAWINGS

FIG. 2 is a longitudinal cross section of a distal end of a catheter, in accordance with an embodiment of the present invention;

DETAILED DESCRIPTION OF EMBODIMENTS

Various medical systems use catheters and other intra-body probes for guiding medical tools and/or administering substances into a patient's body. In some systems, the intra-body probe comprises a position sensor, which enables the system to track the position of the probe inside the body. For example, the position sensor may comprise multiple magnetic field transducers.

Embodiments of the present invention provide medical probes having improved mechanical configurations. In the disclosed configurations, the field transducers are mounted in the probe such that their axes are oriented obliquely with respect to the longitudinal axis of the probe. The term "obliquely oriented" in this context means that the axes of the transducers are neither parallel with nor perpendicular to the longitudinal axis of the probe. In a typical implementation, the position sensor comprises three field transducers, which are substantially mutually orthogonal.

The angles at which the transducers are oriented enable the position sensor to sense three-dimensional magnetic field components, while at the same time preserving a large-diameter unobstructed lumen around the longitudinal axis of the probe. This lumen can be used for any suitable purpose, such as for insertion of medical tools. In an example configuration that is described below, three transducers, each 0.8 mm long, are mounted in a catheter that is less than 3 mm in diameter. This configuration preserves an unobstructed lumen having a diameter of 1.2 mm.

System Description

Figure 1:
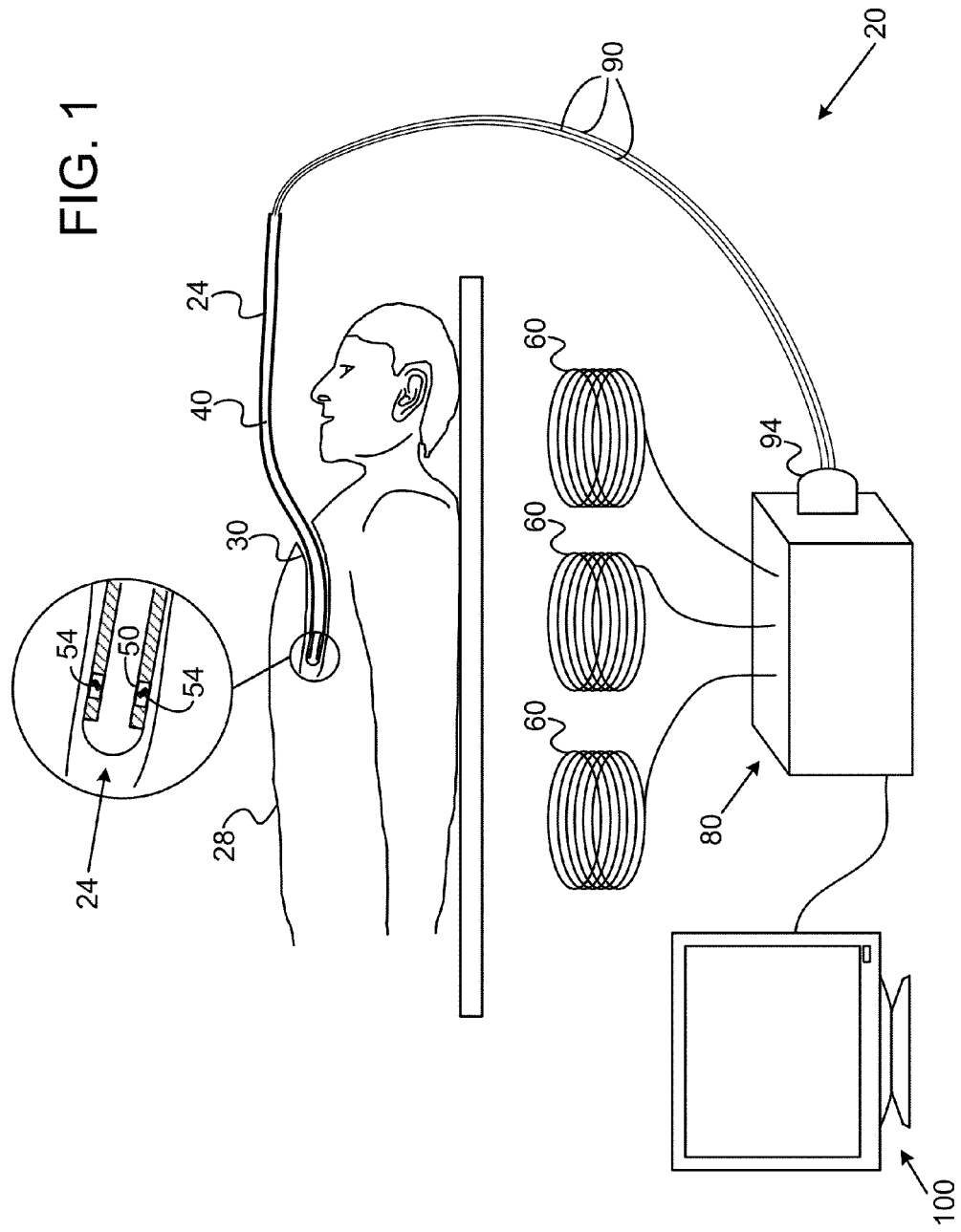
FIG. 1 is a schematic, pictorial illustration of a medical position tracking system, in accordance with an embodiment of the present invention.

FIG. 1 is a schematic, pictorial illustration of a medical position tracking system 20, in accordance with an embodiment of the present invention. In system 20, a medical probe, such as a catheter 24, is inserted into the body of a patient 28, typically through an artery 30. For example, the catheter may be inserted into the patient's heart in order to perform a certain medical procedure. Alternatively, the catheter can be inserted into any other suitable organ.

Catheter 24 comprises an elongate cylindrical body, which defines a central lumen 40 extending in the longitudinal direction of the catheter. Lumen 40 is used for different purposes in different catheter applications. For example, in angioplasty, a balloon can be inflated using saline solution that is conveyed through the lumen. In other applications, various types of medicine or radio-opaque substances can be administered into the organ through the lumen. Alternatively, the lumen can be used for guiding various tools or instruments, such as optical fibers or ablation electrodes.

The distal end of catheter 24 comprises a position sensor 50 for measuring the location and orientation of the catheter inside the patient's body. In some embodiments, position sensor 50 comprises multiple magnetic field detectors 54, e.g., coils, which detect magnetic fields in their vicinity. The magnetic fields are produced by magnetic field generators 60 located at known positions externally to the patient. Field generators 60 are driven by a central unit 80. Each field generator 60 is typically driven by a distinguishable alternating current, so as to generate a distinguishable alternating magnetic field. The alternating currents are typically distinguishable with regard to frequency, phase, time, or combinations thereof.

The magnetic fields produced by generators 60 are detected by field detectors 54 in position sensor 50. The field detectors produce electrical signals that are indicative of the sensed magnetic fields. Leads 90 carry the electrical signals from the field detectors to central unit 80. The leads connect to unit 80 using a connector 94. Based on the electrical signals produced by field detectors 54, central unit 80 calculates the location and the orientation of position sensor 50 (i.e., of the distal end of the catheter) with respect to field generators 60. This position information is typically displayed to an operator, e.g., on a display 100. Further aspects of position tracking of intra-body objects using magnetic field measurements are described in U.S. Pat. No. 6,690,963, cited above.

In the description above, the position sensor comprises field detectors, and the field generators are located externally to the patient body. In alternative embodiments, the position sensor may comprise field generators, and the field detectors may be located externally to the patient body. Both field detectors and field generators are referred to herein as field transducers.

Obliquely-Oriented Field Transducer Configurations

As noted above, lumen 40 in catheter 24 is used for inserting various objects or substances into the patient's body. On one hand, it is highly desirable to preserve a large-diameter unobstructed lumen for these purposes. On the other hand, any component contained in the distal end of the catheter may potentially obstruct this lumen and reduce its diameter.

In particular, field detectors 54 are mounted in the distal end of catheter 24, and may reduce the diameter of the unobstructed lumen. Orienting the field detectors imposes a performance trade-off between position tracking performance and lumen obstruction, since the field detectors should typically be oriented at different angles in order to sense different components of the magnetic field.

Embodiments of the present invention provide improved configurations for mounting magnetic field transducers, such as field detectors 54, in medical probes such as catheter 24. In the configurations described herein, the field transducers are oriented so that their axes are oriented obliquely (i.e., not parallel and not perpendicular) with respect to the longitudinal axis of the probe. As such, the diameter of unobstructed lumen 40 around the longitudinal axis of the probe is increased.

FIG. 2 is a longitudinal cross section of the distal end of catheter 24, in accordance with an embodiment of the present invention. Position sensor 50 is shown located at the distal end of the catheter. As can be seen in the figure, the catheter comprises an elongate cylindrical body 104. The elongate body comprises an insertion tube for insertion into the patient body. The insertion tube defines central lumen 40. Position sensor 50 in the present example comprises a cylinder having a central opening, and lumen 40 of the catheter passes through the central opening of the position sensor.

Position sensor 50 comprises a plurality of magnetic field detectors 54, typically three detectors, two of which are shown in FIG. 2. Detectors 54 typically comprise coils wound on air cores, but may alternatively comprise other types of field detectors. Detectors 54 are mounted around the central opening of position sensor 50, so as not to obstruct lumen 40. Each detector 54 has a respective axis 120, and the detectors are mounted so that their axes are oriented obliquely with respect to a longitudinal axis 130 of the catheter. As a result, detectors 54 are able to sense the three-dimensional components of the magnetic field, while at the same time preserving a large-diameter unobstructed lumen at the center of the catheter. As can be seen in the figure, none of the detectors intersects the central axis of the catheter or obstructs lumen 40 in any way.

In some embodiments, field detectors 54 are assembled and potted in a hollow cylindrical fixture, to form the shape of sensor 50 shown in FIG. 2. The fixture is fitted into the distal end of catheter 24.

Figure 3A:
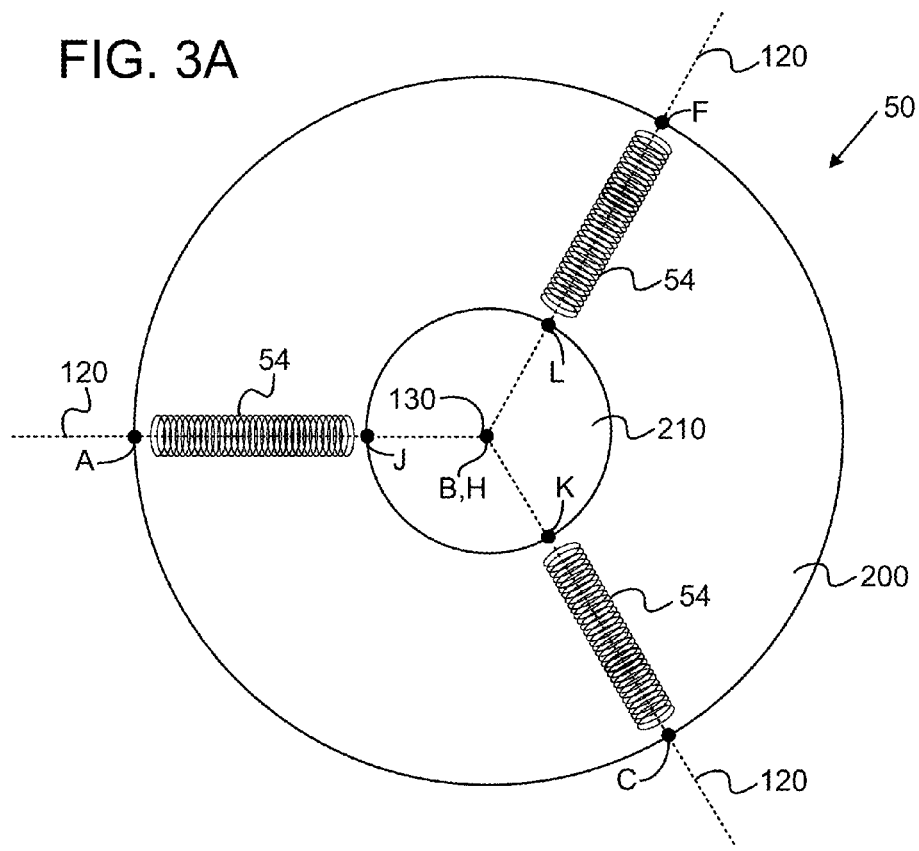
FIGS. 3A and 3B are a cross sections of a position sensor, in accordance with an embodiment of the present invention.
Figure 3B:
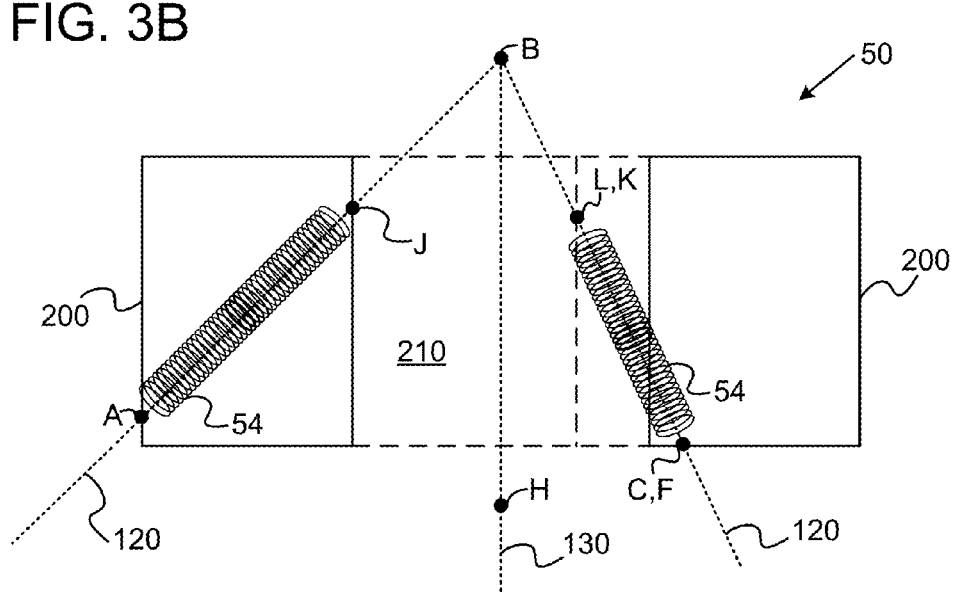

FIGS. 3A and 3B are diagrams showing cross sections of position sensor 50, in accordance with an embodiment of the present invention. FIG. 3A shows a front view, or a transversal cross section, of the position sensor. FIG. 3B shows a longitudinal cross section of the position sensor. Position sensor 50 comprises a cylinder 200 having a central opening 210, such that lumen 40 shown in FIG. 2 above passes through this central opening. Detectors 54 are located around central opening 210, and do not obstruct the lumen. Furthermore, axis 120 of each detector 54 is oriented obliquely with respect to longitudinal axis 130 of the catheter.

Figure 4:
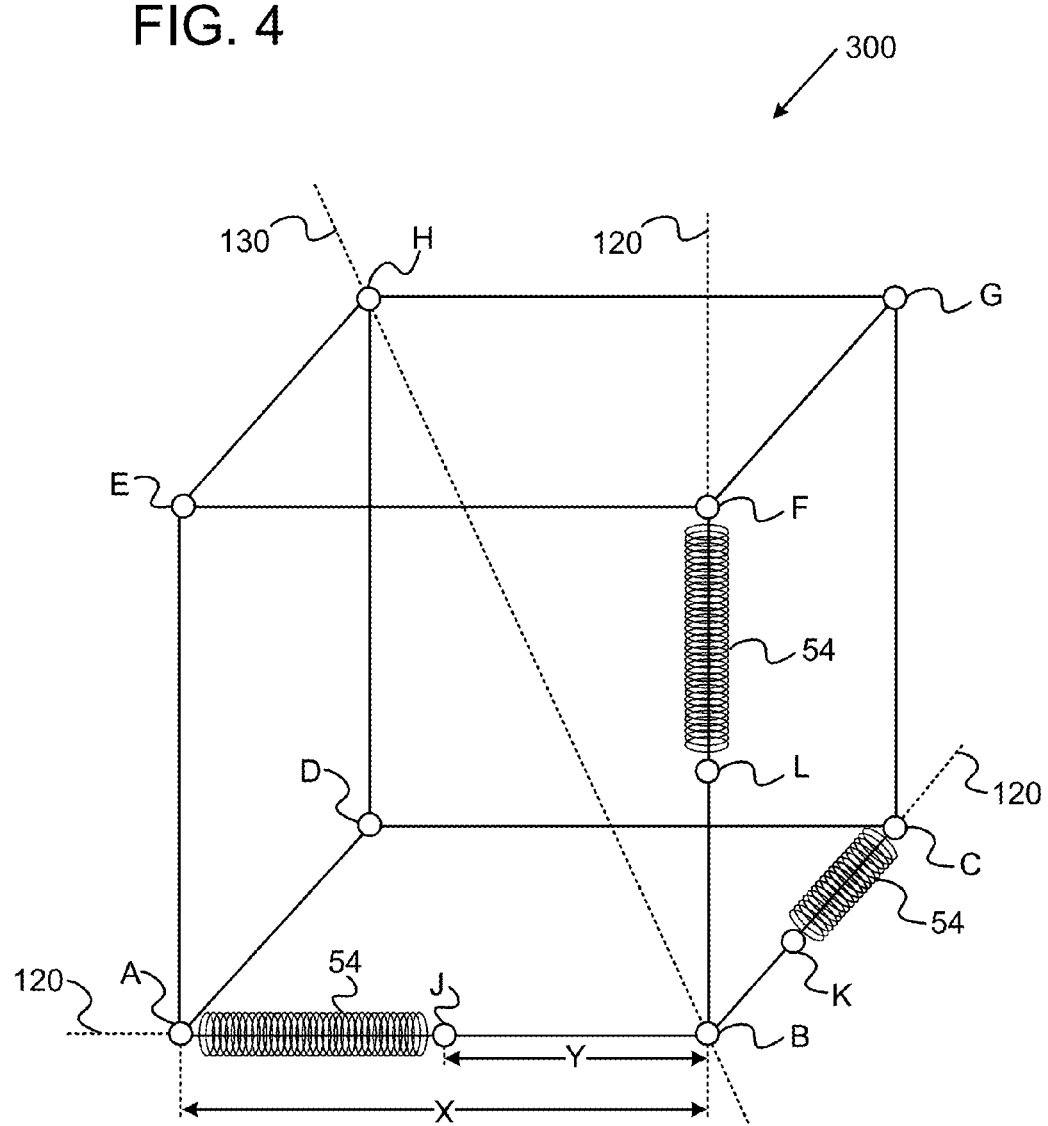
FIG. 4 is a diagram showing a three-dimensional arrangement of field transducers in a position sensor, in accordance with an embodiment of the present invention.

In the present example, detectors 54 are located symmetrically around central opening 210 (i.e., around the longitudinal axis of the catheter), and central axis 120 of each detector 54 is oriented at an angle of approximately 55° with respect to longitudinal axis 130. In this embodiment, central axes 120 of detectors 54 are substantially mutually orthogonal, as illustrated in FIG. 4 below. Three segments along the axes of detectors 54 are denoted in FIGS. 3A and 3B as AJ, FL, and CK, and two points are denoted as B and H. These segments and points are used to correlate the cross sections of FIGS. 3A and 3B with the three-dimensional view of FIG. 4 below.

FIG. 4 is a diagram showing a three-dimensional arrangement of field detectors 54 in position sensor 50, in accordance with an embodiment of the present invention. FIG. 4 shows a virtual cube 300, whose vertices are denoted A . . . H. ABCD and EFGH denote the lower and upper faces of the cube, respectively, and the length of each edge of the cube is denoted x. Three points J, K and L are located on the edges AB, CB and FB, respectively, at a distance y from the common vertex B, wherein y<x. Since the axes of the three detectors lie on three edges of a cube having a common vertex, they are mutually orthogonal.

Now envision that cube 300 is rotated so that diagonal BH coincides with longitudinal axis 130 of the catheter in FIGS. 3A and 3B. (After rotation, points A . . . H in FIG. 4 coincide with the corresponding points marked in FIGS. 3A and 3B.) Detectors 54 are now located so that their central axes 120 coincide with segments AJ, CK, and FL. Thus, FIG. 4 shows that axes 120 of detectors 54 in FIGS. 3A and 3B are mutually orthogonal.

The above description refers to embodiments in which the probe comprises a central lumen, and in which field transducers are arranged so as not to obstruct this lumen. More generally, the techniques described herein can be applied in cases where it is desirable that none of the transducers intersects the longitudinal axis of the probe. For example, the disclosed configurations can be applied in a probe having a cylindrical core that extends in the longitudinal axis of the probe, where it is desired not to disrupt the continuity of the central core.

It will thus be appreciated that the embodiments described above are cited by way of example, and that the present invention is not limited to what has been particularly shown and described hereinabove. Rather, the scope of the present invention includes both combinations and sub-combinations of the features described hereinabove, as well as variations and modifications thereof which would occur to persons skilled in the art upon reading the foregoing description and which are not disclosed in the prior art.

What is claimed is:

1. A medical probe, comprising:
   an elongate body having a longitudinal axis and a central lumen about the longitudinal axis for a passage of solution, substances or objects therethrough; and
   a plurality of magnetic field transducers, which are contained within the body, each magnetic field transducer having a respective magnetic field transducer axis that is oriented obliquely with respect to the longitudinal axis, wherein each magnetic field transducer is positioned along the respective magnetic field transducer axis so as not to interfere with the longitudinal axis and preserving an unobstructed lumen for the central lumen for the passage of solution, substances or objects therethrough and whereby the lumen does not pass through any of the magnetic field transducers.

2. The probe according to claim 1, wherein the elongate body comprises an insertion tube for insertion into an organ of a patient.

3. The probe according to claim 1, wherein the plurality of transducers comprises three transducers.

4. The probe according to claim 3, wherein the transducers are substantially mutually orthogonal.

5. The probe according to claim 1, wherein the transducers are positioned within the elongate body so that none of the transducers intersects the longitudinal axis.

6. The probe according to claim 1, wherein the transducers are positioned at a distal end of the elongate body, and wherein the probe comprises leads connecting the transducers to a connector located at a proximal end of the elongate body.

7. The probe according to claim 1, and comprising a cylinder-shaped fixture for holding the transducers within the elongate body, wherein the fixture has a central opening that is parallel with the longitudinal axis.

8. The probe according to claim 1, wherein the field transducers comprise coils.

9. A medical position tracking system, comprising:
   a medical probe, comprising:
      an elongate body having a longitudinal axis and a central lumen about the longitudinal axis for a passage of solution, substances or objects therethrough; and
      a plurality of magnetic field transducers, which are contained within the body, each magnetic field transducer having a respective magnetic field transducer axis that is oriented obliquely with respect to the longitudinal axis, wherein each magnetic field transducer is positioned along the respective magnetic field transducer axis so as not to interfere with the longitudinal axis and preserving an unobstructed lumen for the central lumen for the passage of solution, substances or objects therethrough and whereby the lumen does not pass through any of the magnetic field transducers; and
   a position measurement subsystem, which is arranged to exchange one or more magnetic fields with the magnetic field transducers in the probe, and to compute a position of the probe responsively to the exchanged fields.

10. The system according to claim 9, wherein the elongate body comprises an insertion tube for insertion into an organ of a patient.

11. The system according to claim 9, wherein the plurality of transducers comprises three transducers.

12. The system according to claim 9, wherein the transducers are substantially mutually orthogonal.

13. The system according to claim 9, wherein the transducers are positioned within the elongate body so that none of the transducers intersects the longitudinal axis.

14. The system according to claim 9, wherein the transducers are positioned at a distal end of the elongate body, wherein the probe comprises leads connecting the transducers to a connector located at a proximal end of the elongate body, and wherein the probe connects to the position measurement subsystem using the connector.

15. The system according to claim 9, wherein the probe comprises a cylinder-shaped fixture for holding the transducers within the elongate body, and wherein the fixture has a central opening that is parallel with the longitudinal axis.

16. The system according to claim 9, wherein the transducers comprise field detectors, which are positioned at a distal end of the elongate body and are operative to sense one or more magnetic fields generated by the position measurement subsystem in a vicinity of the distal end and to produce, responsively to the sensed fields, respective electrical signals that are indicative of the position of the distal end.

17. The system according to claim 9, wherein the transducers comprise field generators, which are positioned at a distal end of the elongate body and are operative to generate one or more magnetic fields for sensing by the position measurement subsystem, such that the fields sensed by the position measurement subsystem are indicative of the position of the distal end.

* * * * *